(12) United States Patent
Sanders

(10) Patent No.: US 7,807,905 B2
(45) Date of Patent: Oct. 5, 2010

(54) **TRAILING GROWTH HABIT IN *IMPATIENS***

(75) Inventor: Monica Maria Adelheid Sanders, Grootebroek (NL)

(73) Assignee: Syngenta Participations AG, Basel (CH)

( * ) Notice: Subject to any disclaimer, the term of this patent is extended or adjusted under 35 U.S.C. 154(b) by 376 days.

(21) Appl. No.: 11/051,278

(22) Filed: Feb. 4, 2005

(65) Prior Publication Data

US 2005/0177905 A1 Aug. 11, 2005

(30) Foreign Application Priority Data

Feb. 6, 2004 (GB) ................. 0402658.9

(51) Int. Cl.
*A01H 5/00* (2006.01)
*A01H 5/10* (2006.01)
*A01H 1/00* (2006.01)
(52) U.S. Cl. .................... 800/323; 800/260; Plt./317
(58) Field of Classification Search ............. 800/260, 800/269, 323; Plt./317
See application file for complete search history.

(56) References Cited

U.S. PATENT DOCUMENTS

| PP5,153 P | 12/1983 | Mikkelsen | Plt./68 |
|---|---|---|---|
| 5,986,188 A * | 11/1999 | Leue | 800/323 |
| PP12,340 P2 | 1/2002 | Cosner et al. | Plt./317 |
| PP12,588 P2 * | 4/2002 | Guillen | Plt./317 |
| PP14,207 P2 * | 10/2003 | Danziger | Plt./317 |
| PP14,690 P2 | 4/2004 | Ramirez | Plt./317 |
| PP15,237 P2 | 10/2004 | Jonkers | Plt./317 |
| PP15,244 P2 | 10/2004 | Heffner | Plt./317 |
| PP15,245 P2 | 10/2004 | Heffner | Plt./317 |
| PP15,865 P2 | 7/2005 | Heffner | Plt./317 |
| 6,924,416 B2 | 8/2005 | Guillen | 800/269 |
| 2002/0138883 A1 * | 9/2002 | Guillen | 800/323 |

FOREIGN PATENT DOCUMENTS

WO WO 01/047349 7/2001

OTHER PUBLICATIONS

McGown. Out of Africa: Mysteries of Access and Benefit Sharing, 2006, pp. 1-42.*
Grey-Wilson. 1980. *Impatiens* of Africa: Morphology, pollination and pollinators, ecology, phytogeography, hybridisaton, keys and a systematic treatment of all African species. With a note on collecting and cultivation. Royal Botanic Gardens, Kew, A.A. Balkema, Rotterdam, pp. 8, 78-91, 227 and 228.*
Guillen. Trailing interspecific *Impatiens*. WO 01/047349, Jul. 5, 2001.*
C. Greg-Wilson, *Impatiens* of Africa: Morphology, pollination and pollinators, ecology, phytogeography, hybridisation, keys and a systematic treatment of all African species With a note on collecting and cultivation. Royal Botanic Gardens, Kew, A.A. Balkema, Rotterdam, 1980.
BallFloraPlant® Fanfare™ Trailing *Impatiens* Culture Information. [online]. [retrieved on Apr. 23, 2004] Retrieved from the Internet: http://www.ballfloraplant.com.

* cited by examiner

*Primary Examiner*—Medina A Ibrahim
*Assistant Examiner*—Keith O. Robinson
(74) *Attorney, Agent, or Firm*—S. Matthew Edwards

(57) ABSTRACT

The instant invention relates to an Impatiens plant having a trailing growth habit during its vegetative and generative growth phase. The invention particularly relates to such plants belonging to the African group of ornamental Impatiens. The invention further relates to pollen, seed and sexual as well as asexual progeny of such plants, to methods for obtaining Impatiens plants with a trailing growth habit, to methods for propagating said plants and to uses of said plants.

9 Claims, No Drawings

TRAILING GROWTH HABIT IN *IMPATIENS*

CROSS-REFERENCE TO RELATED APPLICATIONS

This application claims the benefit of GB 0402658.9, filed Feb. 6, 2004. The above application is incorporated herein by reference in its entirety.

The instant invention relates to an Impatiens plant having a trailing growth habit during its vegetative and generative growth phase. The invention particularly relates to such plants belonging to the African group of ornamental Impatiens. The invention further relates to pollen, seed and sexual as well as asexual progeny of such plants, to methods for obtaining Impatiens plants with a trailing growth habit, to methods for propagating said plants and to uses of said plants.

The genus Impatiens belongs to the family Balsaminaceae and is comprised of about 1000 species of annual or perennial herbs or sub-shrubs, which are widely distributed in the tropics and subtropics of Asia and Africa. Numerous representatives of this genus are cultivated as ornamental plants and several are of significant commercial importance. Most of the commercial Impatiens cultivars are derived either from the group of the New Guinea Impatiens or from the African Impatiens. For commercial production, New Guinea Impatiens are usually propagated asexually by cuttings while the African Impatiens can be propagated sexually by seed or asexually by cuttings.

*I. walleriana*, commonly known as Touch-Me-Not or Busy Lizzy, is of particularly high commercial interest. It belongs to the African Impatiens and is widely used as annual ornamental plant for bedding, pot culture and hanging baskets. *I. walleriana* is a species aggregate of about nine species of rather succulent perennial plants which are native of East Tropical Africa. The plants are widespread and occur in a number of localities from southeast Kenya to Mozambique and southern Malawi. They are generally variable, ca. 30-70 (–80) cm tall with simple or branched, thick, fleshy, pale green stems which are occasionally rooting at the lower nodes (C. Grey-Wilson, Impatiens of Africa, A. A. Balkema, Rotterdam, 1980).

*I. usambarensis* is a rather robust, up to 2 m tall, upright growing plant which is native of the Usambara Mountains in Tanzania. *I. usambarensis* has no commercial significance. The habitats and distribution areas of *I. usambarensis* and *I. walleriana* are partially overlapping and naturally occurring interspecific hybrids have been described (C. Grey-Wilson, Impatiens of Africa, A. A. Balkema, Rotterdam, 1980), although crosses of cultivated plants generally do not yield viable seeds.

A trailing growth habit is a highly desired trait for commercial ornamental Impatiens plants. However, far most commercial Impatiens cultivars grow upright and do not show trailing characteristics. From the New Guinea Group of ornamental Impatiens only plants with a semi-procumbent or procumbent growth habit are known, e.g. from US PP 5,132; US PP 5,134 and US PP 4,262. New Guinea Impatiens plants reported in the art to exhibit a trailing-type growth habit are either more similar to those of the semi-procumbent New Guinea Impatiens (US PP 7,098) or loose the would-be trailing characteristic after the transition to the generative growth phase (WO 01/47349 and US2002/0138883 A1).

It is thus desirable to provide a real and lasting trailing growth habit in a broad range of species and cultivars of ornamental Impatiens, wherein the trailing growth habit is preferably also maintained after the transition to flowering, throughout the generative growth of the plants. Such plants extend the spectrum of possible uses of ornamental Impatiens in the gardening industry and are more appealing to the consumer.

The main objective of the invention is therefore to provide an ornamental Impatiens plant having a trailing growth habit during its vegetative and generative growth phase. Another objective of the invention is to provide a trailing Impatiens plant belonging to the African group of ornamental Impatiens. A further objective of the invention is to provide methods for obtaining plants according to the invention.

Within the meaning of the present invention, a trailing growth habit is a growth habit of a plant, wherein the stems and lateral branches of the plant grow in predominantly horizontal orientation. The trailing type plant according to the invention may, optionally, also shows a high degree of branching which is usually higher than that found in non-trailing type cultivars. If grown in the confinement of a plant container, the plant will extend over the container and, when reaching the edge of the container, also grow towards the ground. The internodes of a trailing-type plant according to the invention may optionally comprise adventitious roots, which are especially built at positions where the internodes get into contact with the substrate. Under favourable environmental conditions, herein after referred to as rooting conditions, the formation of adventitious roots is enhanced and may also occur without contact to the substrate.

Rooting conditions within the meaning of the present invention are characterised by moist substrate and temperatures of between 14° C. to 30° C., specifically of between 16° C. to 25° C., more specifically of between 17° C. to 22° C., but especially of between 18° C. to 20° C. The night temperatures should not go below 14° C. and the air humidity under the plants should be in a range of between 65% and 100%, but specifically between 70% to 100%, more specifically between 85% to 95% and even more specifically between 85% to 90%.

If grown in the field under the above rooting conditions the trailing habit becomes even more pronounced. Adventitious roots enhance the capacity of water and nutrient uptake and enable the plant to grow more vigorously and at a higher rate and, thus, to stretch out more rapidly than non-trailing plants.

The present invention relates to an Impatiens plant having a trailing growth habit, wherein the trailing growth habit is maintained during the generative growth of the plant.

A specific embodiment of the invention relates to an Impatiens plant having a trailing growth habit, wherein the trailing growth habit is maintained during the generative growth of the plant, and wherein the plant is belonging to the species *Impatiens walleriana*.

In a further embodiment the plant according to the invention has a high degree of lateral branching which is substantially higher than that found in non-trailing type cultivars, even in cases wherein both plants have otherwise a similar genetic background.

By "substantially higher", the number of branches in a trailing type plant according the invention is meant to be at least about 1.3 times, especially at least about 1.9 times, specifically between about 1.3 and about 2.5 times, more specifically between about 1.8 and about 2.2 times, but especially between about 1.9 and about 2.1 times higher than that found in a non-trailing type cultivar, which otherwise has a similar genetic background, especially if plants are cultivated under commercial conditions.

In a further embodiment the trailing plant according to the invention, when grown under commercial conditions, has at least about 1.5 times, specifically at least about 2.0 times, but typically between about 1.5 to about 3.5 times, specifically between about 1.6 to about 2.5 times, and more specifically about 2.5 times more flowers than a reference plant having a non-trailing growth habit, wherein both plants have otherwise a similar genetic background.

Within the meaning of the present invention, a plant with a "similar genetic background" refers to a plant, that is genetically closely related to a plant according to the invention and may be a parent in the pedigree of a plant according to the invention, such as, for example, CAJUN® or IMPULSE®.

In a further embodiment of the invention, the lateral shoots or branches are capable of forming adventitious roots at their internodes, especially when getting into contact with the substrate.

In a further embodiment the trailing plant according to the invention, is obtainable from a cross, wherein at least one of the parents is *Impatiens usambarensis* x *walleriana*.

In a specific embodiment the plant according to the invention has between about 14 and about 17 weeks, especially between about 15 and about 16 weeks, but specifically about 16 weeks after sowing a ratio between plant height and plant diameter, which is less than about 0.39, but typically between about 0.3 and about 0.4, specifically between about 0.3 and about 0.38, and more especially between about 0.3 and about 0.33, if plants are grown in the confinement of a plant container. For plants grown in the field for about 14 and about 17 weeks, especially between about 15 and about 16 weeks, but specifically about 16 and about 17 weeks after planting, the ratio between plant height and plant diameter is less than about 0.36, but typically between about 0.15 and about 0.35, specifically between about 0.20 and about 0.30, more specifically between about 0.20 and about 0.28, but especially about 0.23.

In a further embodiment the trailing plant according to the invention, when cultivated for 16 weeks under commercial conditions, comprises up to about two times more branches than a reference plant having a non-trailing growth habit, wherein both plants have otherwise a similar genetic background.

In a further embodiment the trailing plant according to the invention, when grown for between about 14 and about 17 weeks, especially for between about 15 and about 16 weeks, but specifically for about 16 weeks under commercial conditions, comprises about 1.5 to about 3.5 times more flowers than a reference plant having a non-trailing growth habit, even in cases wherein both plants have otherwise a similar genetic background such as, for example, CAJUN® or IMPULSE®.

In a specific embodiment the plant according to the invention has between about 14 and about 17 weeks, especially between about 15 and about 16 weeks, but specifically about 16 weeks after sowing a ratio between plant height and plant diameter, which is less than about 0.45 and comprises at least about 1.3 times more branches than a reference plant having a non-trailing growth habit, wherein both plants have otherwise a similar genetic background such as, for example, CAJUN® or IMPULSE®.

In a specific embodiment the plant according to the invention has between about 14 and about 17 weeks, especially between about 15 and about 16 weeks, but specifically about 16 weeks after sowing a ratio between plant height and plant diameter, which is less than about 0.45 and comprises at least about 1.5 times more flowers than a reference plant having a non-trailing growth habit, wherein both plants have otherwise a similar genetic background such as, for example, CAJUN® or IMPULSE®.

In a further embodiment the trailing plant according to the invention has a flower colour pattern selected from the group consisting of single colour, bicolour and striped.

In a further embodiment the trailing plant according to the invention has a double flower.

In a specific embodiment the trailing *Impatiens walleriana* plant according to the invention is typified by *Impatiens walleriana* JN 215 which was deposited at NCIMB Ltd. under accession number NCIMB 41210 on Feb. 5, 2004.

A further embodiment of the invention are sexual progeny of trailing Impatiens plants, including seed, of a plant according to the invention.

A further embodiment of the invention is pollen, ovule or embryo of trailing Impatiens plants according to the invention.

A further embodiment of the invention is a method of introgressing a trailing growth habit into a plant of the species *Impatiens walleriana* comprising the steps of
  a) generating a cross between *Impatiens usambarensis* x *walleriana* and *I. walleriana*;
  b) rescuing a viable embryo resulting from the cross of step a);
  c) regenerating the rescued embryo of step b) into a plant;
  d) backcrossing said regenerated plant or a sexual or asexual progeny of said plant with *Impatiens walleriana*, wherein this step may optionally be repeated at least once;
  e) selecting a plant having a trailing growth habit from the plants obtained by backcrossing in step d) or from sexual or asexual progeny of such plants.

A further embodiment of the invention is a method of selecting trailing *Impatiens walleriana* plants according to the invention comprising the steps of
  a) growing back crossed *Impatiens walleriana* plants obtained in step d) above or sexual or asexual progeny thereof in rows in a field, wherein the distance between the rows is at least 80 cm; and
  b) selecting an individual plant or a group of plants which is capable of covering the free area between the rows significantly faster than the average of all plants grown in step a).

A further embodiment of the invention is an *Impatiens walleriana* plant having a trailing growth habit which is obtainable by a method as described above.

A further embodiment of the invention is a method of producing seed of a plant having a trailing growth habit comprising the steps of
  a) obtaining a trailing plant according to the invention;
  b) allowing said plant of step a) to i) self-pollinate or ii) sib pollinate or iii) cross-pollinate; and
  c) harvesting seed resulting from step b).

A further embodiment of the invention is a method of producing a plant having a trailing growth habit comprising the steps of
  a) obtaining a trailing plant according to the invention; and
  b) asexually propagating said plant of step a).

A further embodiment of the invention is a method of producing a plant having a trailing growth habit comprising the steps of
  a) planting a seed of a trailing plant according to the invention; and
  b) growing said plant of step a).

In one embodiment, said seed planted in step a) above is planted in a container or in a field.

A further embodiment of the invention is the use of a plant according to the invention for creating an ornamental arrangement.

A specific embodiment of the invention is the use of a plant according to the invention for creating an ornamental arrangement in a hanging basket.

A specific embodiment of the invention is the use of a plant according to the invention for creating an ornamental arrangement, wherein said plant is combined with at least one medium fast growing ornamental plant.

A further embodiment of the invention is an ornamental arrangement comprising a plant according to the invention.

A further embodiment of the invention is an ornamental arrangement in a hanging basket comprising a plant according to the invention.

Trailing Impatiens plants according to the invention can be obtained from crosses within the genus *Impatiens*, especially from crosses between African and New Guinea *Impatiens*.

In a further embodiment, the Impatiens plants according to the invention can be obtained from crosses between species or hybrids belonging to the African group of Impatiens. In a specific embodiment of the invention, trailing Impatiens plants are obtainable from a cross between the naturally occurring hybrid *I. usambarensis* x *walleriana* and ornamental *I. walleriana*, wherein both crossing partners can be used as male or as female parent.

In Impatiens, interspecific crosses or crosses involving interspecific hybrids often result in an abort of the embryo, especially when the parent plants are of a different geographic origin. Viable embryos resulting from such crosses can be rescued by methods generally known in the art and germinated in vitro. Methods for embryo rescue, which are specifically optimised for Impatiens were described by T. Arisumi (J. Amer. Soc. Hart. Sci. 105(5): 629-631, 1980).

Though progeny obtained by embryo rescue are often sterile and can then only be propagated asexually by cuttings, it is also possible to find fertile plants among them, which set seed after self-pollination or which can be used as either male or female parent in a cross with another Impatiens plant.

In a preferred embodiment of the invention the naturally occurring interspecific hybrid *I. usambarensis* x *I. walleriana* is crossed with *I. walleriana* and sexual progeny of the F1 plants resulting from said cross are obtained by self-pollination. The resulting F2 plants or sexual or asexual progeny thereof are grown in the field and are selected for a trailing growth habit. In a preferred embodiment the F2 plants or sexual or asexual progeny thereof are grown in the field in rows, wherein the distance between the rows is at least 80 cm. Trailing plants typically stay lower than non-trailing plants. Furthermore, trailing plants are capable of covering the free area between the rows significantly faster than the average of all plants grown in the row and can thus be efficiently selected.

The selected plants having a trailing growth habit can then be further propagated sexually or asexually by methods generally known in the art.

In a preferred embodiment the selected plants having a trailing growth habit are crossed to other Impatiens plants with a desired genetic background, preferentially to ornamental Impatiens cultivars. Trailing plants are then selected among the progeny and, optionally, the resulting F1 plants are backcrossed to one of the parent plants, preferably to the ornamental Impatiens cultivar, or self-pollinated.

Trailing ornamental Impatiens lines, hybrids or cultivars for asexual propagation can be obtained from such material by applying breeding and selection schemes generally known in the art.

It is well known to the skilled person, that the choice of the plant material which is crossed to the trailing material of the invention is generally determinative for the phenotypic characteristics of the progeny, for example for features like leaf colour, flower colour and flower type. Trailing monochrome, bicolour or striped Impatiens plants or Impatiens plants having a double flower can be obtained by backcrossing trailing plants with an inbred line having said features as the recurrent parent.

In a specific embodiment of the invention, the resulting F1 plants are crossed with the recurrent parent one or several times to replace more of the genome of the Impatiens parent providing the trailing habit trait, particularly between 80% to 99.5% of the genome, more particularly between 90% and 99% of the genome, but especially between 95% and 98% of the genome. In every generation, the presence or absence of the trailing trait must be determined. Due to the growth characteristic of the plants expressing the trailing trait, the presence or absence of this trait in the progeny plants can be easily detected by visual scoring.

After the last backcross generation a selfing step is required.

In another embodiment the trailing plants are backcrossed with Impatiens plants belonging to the African group of ornamental Impatiens, more specifically to *I. walleriana*.

Trailing Impatiens plants according to the invention can be crossed with plants belonging to colour series of Impatiens plants, which are already well established on the market, allowing to establish a similar colour series of trailing Impatiens plants. Examples for colour series of *I. walleriana* cultivars with monochrome flower are CAJUN® or IMPULSE®, examples for cultivars having a bicolour flower are "Florette Star" and examples for cultivars having a double flower with an enhanced number of petals are "Fiesta" (S & G Ornamental Flowers Catalogue 2004).

Trailing Impatiens plants according to the invention can also be crossed with plants having a striped colour patter as described in WO0042837. This colour pattern is described for New Guinea Impatiens Electra Tie Dye (U.S. Pat. No. 6,353, 162) but it is also found in *I. walleriana*.

In another embodiment, trailing Impatiens plants according to the invention are crossed to related Impatiens plants of a different geographic origin. If required, viable embryos of such crosses can be rescued and regenerated in vitro applying methods generally known in the art. In case where the in vitro germinated plant is sterile, it can be propagated asexually, e.g. by cuttings. In a preferred embodiment, the trailing plant belongs to the African group of ornamental Impatiens, preferably to *I. walleriana* and the related crossing partner of different geographic origin belongs to the New Guinea group of Impatiens. In another preferred embodiment, said New Guinea Impatiens has flowers with an enhanced number of petals, e.g. a double flower. In another preferred embodiment, said New Guinea Impatiens has striped flowers.

Trailing Impatiens plants according to the invention generally have a stronger growth vigour than non-trailing Impatiens plants, when grown under the same conditions. This may be due to their ability to form adventitious roots at the internodes of lateral branches, a trait which is often correlated with the trailing growth habit. Adventitious roots enhance the capacity of water and nutrient uptake and enable the plant to grow at a higher rate and, thus, to stretch out more rapidly than non-trailing plants. Trailing Impatiens plants are therefore capable of covering a planting container in shorter time than non-trailing, upright growing plants and allow to reduce cultivation time and production costs. Another advantage of plants with a trailing growth habit is that they begin to flower earlier and have more flowers than non-trailing plants grown under the same conditions, especially during the early growth stages. This allows the gardener to sell attractive plants in a very young stage. In bedding use the time required to cover the entire soil surface is lower and the number of plants per area can be reduced when plants with a trailing growth habit are chosen instead of non-trailing plants.

A trailing growth habit according to the invention, which is not only present during the vegetative growth phase but which is maintained also after the transition to flowering, throughout the generative growth phase, is of particular value for gardening industry, because the favourable characteristics of trailing plants are maintained also during the growth of the plant at the end-customer. Trailing Impatiens plants according to the invention thus extend the spectrum of possible uses of Impatiens plants for gardeners. They are capable of entirely covering a hanging basket from all sides, including the bottom, after relatively short cultivation time, what can not be achieved with upright growing plants. Due to their enhanced growth vigour trailing Impatiens plants can be combined with other ornamental plants in ornamental arrangements, while Impatiens plants with non-trailing growth habit and have a lower growth vigour, are therefore usually less competitive and tend to be overgrown by other plants. Trailing Impatiens plants according to the invention can, for example, be combined with medium strong growing species, such as Bidens solaire compact (Bidtis), Lobelia (Laguna), Sanvitalia (Cuzco), Begonia Maribel, Verbena cuttings (Babylon/Tukana), Argyranthemum (Molimba), Fuchsia hybrids and Scaevola (Saphira/Whirlwind).

Due to their unique characteristics, trailing ornamental Impatiens plants according to the invention extend the spectrum of possible uses of Impatiens in commercial gardening.

Under commercial conditions non-trailing Impatiens plants are typically cultivated for 10-12 weeks in a greenhouse until they are ready for sale.

The term "commercial conditions" hereinafter refers to growth conditions which are typically found in a greenhouse in which Impatiens plants are produced for commercial purposes such as those described, for example, in Vic Ball, Ball Red Book, 16th Edition, Ball Publishing, Batavia Ill. (1998).

Impatiens plants are ready for sale when the plant has filled the pot and is showing flowers.

Trailing ornamental Impatiens plants according to the invention are typically earlier ready for sale than non-trailing plants with a similar genetic background. Thus, trailing Impatiens plants allow to reduce cultivation time and production costs. Alternatively, trailing ornamental Impatiens plants according to the invention have significantly more flowers than non-trailing plants cultivated under the same conditions, allowing the gardener to sell a more attractive product. In a preferred embodiment of the invention trailing Impatiens plants have 1.5-2.5 times more flowers than non-trailing plants when cultivated for 16 weeks under commercial conditions. More preferably, trailing plants have about 1.5-3.5 times more flowers than non-trailing plants.

Trailing Impatiens plants according to the invention are further characterised by a larger plant diameter and a lower plant height than non-trailing Impatiens plants. About 16 weeks after sowing the ratio between plant height and plant diameter is less than 0.39, but typically between 0.3 and 0.4, specifically between 0.3 and 0.38, and especially between 0.3 and 0.33, if plants are grown in the confinement of a plant container. For plants grown in the field for between 14 and 17 weeks, especially between 15 and 16 weeks, but specifically between 16 and 17 weeks after planting, the ratio between plant height and plant diameter is less than 0.36, but specifically between 0.15 and 0.35, more specifically between 0.20 and 0.30, even more specifically between 0.20 and 0.28, but especially 0.23. Furthermore, trailing Impatiens plants according to the invention have more branches than non-trailing plants. The number of branches of trailing plants grown for 16 weeks under commercial conditions is at least 1.3 times, especially at least 1.9 times, but typically between 1.3 and 2.5 times, specifically between 1.8 and 2.2 times, but especially between 1.9 and 2.1 times higher than the number of branches of non-trailing plants.

All references cited herein are incorporated by reference in the application in their entireties.

EXAMPLES

The following examples are intended to provide illustrations of the application of the present invention. The following examples are not intended to completely define or otherwise limit the scope of the invention.

Example 1

Seeds of an accession of *I. usambarensis* x *walleriana* which was cultivated from a wild collection from Tanzania, were obtained from the Royal Botanical Garden Edinburgh under accession no. RBGE 19821569. The material was cultivated and crossed to *I. walleriana*, wherein RBGE 19821569 was used as the female parent and *I. walleriana* as the male parent.

The following *I. walleriana* genotypes were used as pollinators: E1329-1, G2171-1, G2129-1, J475-2, G2099-1 and H1636-1. Embryos resulting from these crosses were rescued and germinated in vitro following the protocol of T. Arisumi (J. Amer. Soc. Hart. Sci. 105(5): 629-631, 1980). In particular, the embryos were obtained between 6 and 12 days after pollination and cultured in a MS medium. A B5 medium supplemented with 4 g/l sucrose was used to start rooting of the embryos.

The germination frequency of the rescued embryos (F1 generation) was typically between 0.0 and 13.5%. The F1 plants were grown in containers in the greenhouse and F2 seeds were obtained from fertile plants upon self pollination. In the following year, the F2 generation was grown in the field and an F3 generation was generated from self-pollination and sister-crosses.

Example 2

The F3 generation of Example 1 was grown in the field in rows with at least 80 cm distance and plants with a trailing growth habit were selected. Trailing plants were sexually propagated by self-pollination or sister-crosses and the progeny were subjected to further selection in the year after. Selected plants with a trailing growth habit were then repeatedly crossed to *I. walleriana*.

The trailing growth habit was observed first in the F3 generation. Most of the selected plants with trailing growth habit originate from the crosses RBGE 19821569 x G2171-1 and RBGE 19821569 x J475-2.

Seed of an *I. walleriana* JN215 resulting from these crosses and comprising a trailing growth habit which is representative for the trailing plants of the invention were deposited under Budapest Treaty with NCIMB Ltd., 23 St. Machar Drive, Aberdeen AB24 3RY under accession number NCIMB 41210 on Feb. 5, 2004.

Furthermore, trailing ornamental *I. walleriana* plants in various colours and with different genetic background have been obtained as indicated in Table 1.

TABLE 1

Genetic background of *I. walleriana* plants of different colour, with introgressed trailing trait.

| Genotype | Colour | Family | Grand Parents | parent with genetics from cross with RBGE 19821569 (F446) |
|---|---|---|---|---|
| V4420 | orange | N2233 | K5218 × L38 | K5218 = F446 × E348 |
| V4442 | pink | P1692 | K5207 × N1556 | K5207 = F446 × F566 |
| V4464 | violet | Q1269 | N2921 × N2920 | N2921 = N2204 × N2205 |
| V4473 | lavender | R2932 | N2194 × N2195 | N2204 = K5207 × L38 |
| | | | | N2205 = K5207 × H 420 |
| | | | | N2920 = N2203 × N2233 |
| | | | | N2203 = K5207 × K97 |
| | | | | N2233 = K5218 × L38 |
| | | | | N2194 = K5207 × H351 |
| | | | | N2195 = K5207 × K86 |

Example 3

Hybrid Cajun salmon, non-trailing, and hybrid JN215, trailing, were grown in a greenhouse under conditions essentially corresponding to commercial conditions. Seedlings of the trial plants were transplanted into containers (9 cm pot) with a standard substrate (Jongkind 3 Dklei) during the 3$^{rd}$ week after sowing. Trailing and non-trailing plants were cultivated next to each other to ensure the comparability of the results.

The plants were regularly supplied with standard fertilizer, the temperature was ca. 20° C. during day time and 18° C. during the night. The daylight was supplemented from 07.00-19:00 with 40 W/m$^2$ when the intensity of the daylight was below 20 W/m$^2$.

Plants were spaced when they were touching one another. Of both entries 22 plants were grown.

The diameter and height of the plants was recorded 14 weeks after sowing. The results are shown in table 2

TABLE 2

Comparison of morphological parameters of non-trailing and trailing *I. walleriana* plants 14 weeks after sowing, plants were grown in a 9 cm pot.

| Genotype | | No. branches | No. flowers | plant diameter [cm] | plant height [cm] | height/ diameter |
|---|---|---|---|---|---|---|
| non-trailing Cajun salmon | average | 8.5 | 14 | 22 | 8.8 | 0.39 |
| | std. dev. | 1.15 | 3.42 | 3.23 | 1.11 | |
| trailing JN215 | average | 18 | 34.32 | 35.09 | 11 | 0.3 |
| | std. dev. | 1.13 | 3.25 | 2.81 | 0.9 | |
| | trailing/ non-trailing | 2.12 | 2.45 | 1.60 | 1.25 | 0.77 |

Example 4

A trial was conducted with different genotypes, wherein 6 individuals of each genotype of the trailing Impatiens plants of Table 1 were grown in a greenhouse under conditions essentially corresponding to commercial conditions and compared to non-trailing plants having the same colours as the trailing plants and a similar genetic background.

The trial was conducted with 6 individuals per colour of the trailing plants and 8 individuals per colour of the non-trailing plants.

Seedlings of the trial plants were transplanted into containers with a standard substrate (Jongkind 3 Dklei) during the 3$^{rd}$ week after sawing. Trailing and non-trailing plants were cultivated next to each other to ensure the comparability of the results.

The plants were regularly supplied with standard fertilizer, the temperature was ca. 20° C. during day time and 18° C. during the night. The daylight was supplemented from 07.00-19:00 with 40 W/m$^2$ when the intensity of the daylight was below 20 W/m$^2$.

In the 16$^{th}$ week after sowing, after the non-trailing plants had reached the maturity for sale, the number of branches, the number of flowers, the length of the branches, the diameter and the height of the plants were recorded for each individual plant. The averages of the results for each genotype and the grand averages and standard deviation for trailing and non-trailing plants are summarised in Table 3.

TABLE 3

Comparison of morphological parameters of non-trailing and trailing *I. walleriana* plants with different genetic background, 16 weeks after sowing. Given are the averages of the individuals per genotype and the grand averages and standard deviations for non-trailing and trailing plants.

| | Genotype | No. branches | No. flowers | length branches [cm] | plant diameter [cm] | plant height [cm] | height/ diameter |
|---|---|---|---|---|---|---|---|
| non-trailing | 4260 | 5.4 | 15.5 | 8.8 | 15.1 | 8.5 | 0.58 |
| | 4290 | 5.1 | 10.3 | 8.6 | 14.6 | 10.0 | 0.70 |
| | 4294 | 5.1 | 12.4 | 8.3 | 15.5 | 10.0 | 0.71 |
| | 4315 | 4.8 | 14.6 | 9.5 | 19.8 | 8.8 | 0.45 |
| | average | 5.1 | 13.2 | 8.8 | 16.3 | 9.3 | 0.61 |
| | std. dev. | 0.3 | 2.4 | 0.5 | 2.4 | 0.8 | 0.12 |
| trailing | V4420 | 9.7 | 24.0 | 6.3 | 18.2 | 7.3 | 0.41 |
| | V4442 | 10.0 | 36.0 | 8.3 | 21.0 | 7.5 | 0.36 |
| | V4464 | 8.0 | 32.8 | 7.7 | 22.0 | 9.2 | 0.43 |
| | V4473 | 12.0 | 36.8 | 7.5 | 22.8 | 7.5 | 0.33 |
| | average | 9.9 | 32.4 | 7.5 | 21.0 | 7.9 | 0.38 |

TABLE 3-continued

Comparison of morphological parameters of non-trailing and trailing *I. walleriana* plants with different genetic background, 16 weeks after sowing. Given are the averages of the individuals per genotype and the grand averages and standard deviations for non-trailing and trailing plants.

| Genotype | No. branches | No. flowers | length branches [cm] | plant diameter [cm] | plant height [cm] | height/diameter |
|---|---|---|---|---|---|---|
| std. dev. | 1.6 | 5.9 | 0.8 | 2.0 | 0.9 | 0.04 |
| trailing/non-trailing | 1.9 | 2.5 | 0.8 | 1.3 | 0.8 | 0.62 |

These measurements were repeated in the 20$^{th}$ week after sowing. These results are summarised in Table 4.

TABLE 4

Comparison of morphological parameters of non-trailing and trailing *I. walleriana* plants with different genetic background, 20 weeks after sowing. Given are the averages of the individuals per genotype and the averages and standard deviations across the genotypes.

| | Genotype | No. branches | No. flowers | length branches [cm] | plant diameter [cm] | plant height [cm] | height/diameter |
|---|---|---|---|---|---|---|---|
| normal type | 4260 | 6.0 | 10.4 | 9.5 | 21.9 | 9.4 | 0.43 |
| | 4290 | 5.8 | 6.8 | 10.1 | 21.1 | 10.1 | 0.48 |
| | 4294 | 5.8 | 5.4 | 9.9 | 23.9 | 8.3 | 0.35 |
| | 4315 | 6.0 | 6.8 | 10.0 | 24.1 | 7.1 | 0.30 |
| | average | 5.9 | 7.3 | 9.9 | 22.8 | 8.7 | 0.39 |
| | std. dev. | 0.1 | 2.1 | 0.3 | 1.5 | 1.3 | 0.08 |
| trailing type | 4420 | 6.8 | 7.0 | 9.0 | 22.7 | 8.2 | 0.36 |
| | 4442 | 7.3 | 10.3 | 10.2 | 25.2 | 7.2 | 0.29 |
| | 4464 | 7.0 | 12.8 | 11.2 | 25.8 | 9.0 | 0.36 |
| | 4473 | 10.0 | 16.3 | 10.7 | 27.0 | 8.3 | 0.32 |
| | average | 7.8 | 11.6 | 10.3 | 25.2 | 8.2 | 0.33 |
| | std. dev. | 1.5 | 3.9 | 0.9 | 1.8 | 0.8 | 0.03 |
| | trailing/normal | 1.3 | 1.6 | 1.0 | 1.1 | 0.9 | 0.84 |

The differences in the height/diameter ratio between normal, non-trailing type cultivars and the trailing type plants according to the invention appear to be less pronounced 20 weeks after sowing. The reason is that plants should have already been spaced out at this point in time. Because of the vigorous growth, the trailing type plants are growing too close to each other. When they touch each other, they stop growing horizontally, which impacts the height/diameter ratio. Also affected is branching and flower set, both of which are lower than expected.

Example 5

In order to overcome the limitations of the "20 week after sowing" experiment described in Example 4, the plants were grown in the field such that any physical limitations impacting horizontal growth and/or branching and flowering of the plants were removed. Plants of *I. walleriana* were raised in the greenhouse in a 12 cm pot and planted in the field 12 weeks after the start of the culture. The plants were then planted in the field with a planting distance of 80 cm between the plants and 120 cm between the rows. The plants were regularly supplied with standard fertilizer and regularly watered in order to keep the surface moist. 17 weeks after planting in the field the diameter and the height of the plants were recorded for each individual plant. The averages of the results for each genotype and the grand averages and standard deviation for trailing and non-trailing plants are summarised in Table 5.

TABLE 5

Comparison of morphological parameters of non-trailing and trailing *I. walleriana* plants with different genetic background, 17 weeks after planting in the field.

| | Genotype | plant diameter [cm] | plant height [cm] | height/diameter |
|---|---|---|---|---|
| non-trailing | Impulse red | 70 | 52 | 0.74 |
| | Fanfare Fuchsia | 65 | 30 | 0.46 |
| | Cajun salmon | 70 | 25 | 0.36 |
| | average | 68.3 | 35.7 | 0.52 |
| | std. dev. | 1.7 | 10.9 | |
| hybrids from seed trailing | (JN215) T1314 | 100 | 25 | 0.25 |
| | trailing/non-trailing | 1.5 | 0.7 | 0.48 |
| hybrids from cutting trailing | Q1794-2 | 100 | 20 | 0.20 |
| | S2705-1 | 80 | 22 | 0.28 |
| | Q1752-1 | 90 | 20 | 0.22 |
| | Q1790-1 | 85 | 19 | 0.22 |
| | S2678-1 | 90 | 22 | 0.24 |
| | average | 89 | 20.6 | 0.23 |

TABLE 5-continued

Comparison of morphological parameters of non-trailing and trailing
*I. walleriana* plants with different genetic background, 17 weeks after
planting in the field.

| Genotype | plant diameter [cm] | plant height [cm] | height/ diameter |
|---|---|---|---|
| std. dev. | 5.2 | 1.12 | |
| trailing/non-trailing | 1.3 | 0.6 | 0.45 |

Example 6

Three seedlings of trailing *I. walleriana* were planted in a 20 cm hanging basked containing standard substrate for bedding plants, cultivated in a greenhouse under commercial conditions, wherein the temperature of the greenhouse was 16-18° C. during day time and 14-16° C. during the night. The plants were regularly supplied with standard fertilizer at a concentration of 0.8 EC at the beginning and 1.5 EC at the end of the cultivation period. The trailing plants were able to fill the hanging basket completely within 20 weeks of cultivation, were hanging down at the sides and were also growing below the basket. As a result, the ornamental arrangement had a spherical appearance and its entire surface was regularly covered with flowers. The basket itself was not visible any more.

Under the identical conditions 5 to 7 non-trailing plants would be required to fill the upper part of the basket but the lower sides and the bottom of the basket would still be visible.

Example 7

An example for an asexually propagated ornamental *I. walleriana* plant having a trailing growth habit can be characterised by the following parameters:

| | |
|---|---|
| Research code: | Q1794-2 |
| Article number: | JM972 |
| Variety name: | Rose |
| Parentage | |
| Female parent: | P2076-2 not patented |
| Male parent: | P1291-4 not patented |
| Propagation | |
| Type cutting: | terminal cuttings |
| Time to initiate roots: | 10-12 days at 20 C. |
| Time to produce a rooted cutting: | 4 weeks |
| Root description: | fine, fibrous and white in colour |
| Plant description | |
| General appearance: | makes long branches that tend to grow horizontally |
| Habit | |
| Growth and branching habit: | freely branching habit, freely flowering, vigorous |
| Crop time | |
| Plant height: | 30 cm |
| Plant spread: | 100 cm |
| Lateral branch description | |
| Length: | 30-37 cm |
| Diameter | 3-4 mm |
| Texture: | smooth, glabrous |
| Internode length: | 0.5-6 cm |
| Colour: | RHS 146C + 184A |
| Foliage description | |
| Arrangement: | alternate/opposite |
| Length, mature leaves: | 5.8-6.6 cm |
| Width, mature leaves: | 3.4-4 cm |
| Shape: | broadly elliptic |
| Apex: | acuminate |
| Base: | acute |
| Margin: | serrate |
| Texture: | smooth, glabrous |
| Venation pattern: | pinnate |
| Colour young foliage, upper surface: | RHS 146B |
| Colour young foliage, lower surface: | RHS 147C + 182B |
| Fully expanded foliage, upper surface: | RHS 146A |
| Fully expanded foliage, lower surface: | RHS 147C + 182B |
| Venation, upper surface: | RHS 146C |
| Venation, lower surface: | RHS 146B |
| Petiole length: | about 1.7-2.5 cm |
| Petiole diameter: | about 2 mm |
| Texture: | smooth, glabrous |
| Colour: | RHS 145B |

-continued

| Flower description | |
|---|---|
| Flower type and flowering habit: | single |
| Number of flowers per leaf axil: | 2 |
| Number of flowers and flower buds per lateral branch: | 15-23 |
| Flower position: | above and beyond the foliage and typically facing upwards and outward |
| Flower shape: | rounded, mostly flat |
| Flowers lasting: | about 7-9 days on the plant depending on environmental conditions |
| Flowers non persistent. | |
| Flowers not fragrant. | |
| Flowering indeterminate and continuous | |
| Flowering season: | Year round under greenhouse conditions. In the garden, flowering from spring until fall |
| Flower diameter: | about 4.5-5.7 cm |
| Flower buds | |
| Rate of opening: | from flower bud to fully open flower, typically about 6-8 days, depending on temperature |
| Bud length (at stage of showing colour): | about 1.5 cm |
| Bud diameter: | about 1 cm |
| Bud shape: | ovoid |
| Texture: | smooth, glabrous |
| Colour, just before opening: | RHS 73A |
| Petals | |
| Quantity: | single, five per flower, imbricate |
| Length of banner petal: | about 1.6-1.9 cm |
| Width of banner petal: | about 2.7-3 cm |
| Length lateral and basal petals: | about 2.6-3.1 cm |
| Width lateral and basal petals: | about 2.4-2.7 cm |
| Lateral and basal petal shape: | obovate |
| Banner petal shape: | broadly obcordate |
| Petal apex: | retuse to emarginate |
| Petal base: | attenuate |
| Petal margin: | entire |
| Petal texture: | smooth, satiny |
| Petal colour: upper surface | when opening and fully opened: RHS N66B |
| middle eye | RHS 46A |
| lower surface | when opening and fully opened: edge: RHS 73A |
| middle | RHS N66D |
| Sepals | |
| Lateral sepals: | 2 |
| Shape: | lineair-lanceolate |
| Apex: | acute |
| Margin: | entire |
| Length: | 3-7 mm |
| Texture upper and lower surface: | smooth, glabrous |
| Spur | |
| Length: | about 3 cm |
| Texture: | smooth, glabrous |
| Aspect: | curved |
| Colour: | RHS 172B |
| Peduncles | |
| Length: | about 2.3 cm |
| Diameter: | 1 cm |
| Aspect: | about 45° from the stem |
| Colour: | RHS 146C |
| Bracts: | at least 2 |
| Shape: | lineair-lanceolate/subulate |
| Apex: | acute |
| Length: | 3-6 mm |
| Colour: | RHS 146A |
| Reproductive organs | |
| Androecium: | stamen number: Five fused at anthers, filaments free, hooded |
| Anther shape: | obovate |
| Anther length: | about 4 mm |
| Anther colour: | RHS 67A |
| Amount of pollen: | no pollen |

-continued

| Gynoecium | |
|---|---|
| Pistil number: | one |
| Pistil length: | about 4 mm |
| Stigma shape: | columnar, five segmented |
| Stigma colour: | red purple |
| Style colour: | RHS 67A |
| Ovary arrangement: | five celled |
| Ovary colour: | RHS 146A |
| Seed development: | seed development has not been observed |
| Disease tolerance: | No known susceptibility to diseases or insects noted to date. |

The invention claimed is:

1. A seed of Impatiens line JN215, wherein a representative sample of seed was deposited under deposit number NCIMB 41210.

2. The Impatiens plant obtained by growing the seed of claim 1.

3. A plant part from the plant of claim 2, wherein the plant part is a root, a stem, a stalk, a leaf, a petal, a silique, pollen, meristem, callus, a sepal, a flower, a cell, tissue or a combination thereof.

4. An asexual progeny of the plant of claim 2.

5. Pollen, ovule or embryo of the plant according to claim 2.

6. An Impatiens plant having all of the physiological and morphological characteristics of the plant of claim 2.

7. A method of producing an Impatiens plant, comprising:
a. crossing an Impatiens plant with the plant of claim 2;
b. obtaining a progeny plant from the cross of step a.

8. The method according to claim 7, further comprising:
c. crossing the progeny plant obtained in step b with and an additional Impatiens plant.

9. The method according to claim 7, further comprising:
c. multiple generations of additional crosses made with the plant obtained in step b via one of the methods selected from the group consisting of outcrossing to an Impatiens plant other than the Impatiens plant used in step a, backcrossing to a parent or grandparent of the plant obtained in step b, and selfing.

* * * * *